(12) United States Patent
Gregoriou et al.

(10) Patent No.: US 11,717,490 B2
(45) Date of Patent: Aug. 8, 2023

(54) THERAPEUTIC NANOCARRIER SYSTEM AND METHODS OF USE

(71) Applicant: UNIVERSITY OF CYPRUS, Nicosia (CY)

(72) Inventors: Yiota Gregoriou, Nicosia (CY); Gregoria Gregoriou, Nicosia (CY); Andreas I. Constantinou, Chicago, IL (US)

(73) Assignee: UNIVERSITY OF CYPRUS, Nicosia (CY)

( * ) Notice: Subject to any disclaimer, the term of this patent is extended or adjusted under 35 U.S.C. 154(b) by 0 days.

(21) Appl. No.: 17/339,339

(22) Filed: Jun. 4, 2021

(65) Prior Publication Data
US 2021/0378978 A1 Dec. 9, 2021

Related U.S. Application Data

(60) Provisional application No. 63/035,415, filed on Jun. 5, 2020.

(51) Int. Cl.
*A61K 9/51* (2006.01)
*A61K 31/05* (2006.01)
*A61K 47/10* (2017.01)

(52) U.S. Cl.
CPC ............ *A61K 9/5146* (2013.01); *A61K 31/05* (2013.01); *A61K 47/10* (2013.01)

(58) Field of Classification Search
CPC ...... A61K 9/5146; A61K 31/05; A61K 47/10; A61K 31/37
See application file for complete search history.

(56) References Cited

U.S. PATENT DOCUMENTS

2005/0142189 A1\* 6/2005 Lambert ............... A61K 47/22
424/456
2017/0035701 A1 2/2017 Sheu et al.

FOREIGN PATENT DOCUMENTS

WO WO-2020002917 A1 \* 1/2020 ............. A61K 31/05

OTHER PUBLICATIONS

International Search Report and Written Opinion for Application No. PCT/EP2021/065053, dated Aug. 13, 2021.
Xiaolong Tang et al., "Co-delivery of docetaxel and Poloxamer 235 by PLGA-TPGS nanoparticles for breast cancer treatment", *Materials Science and Engineering C*, vol. 49, pp. 348-355 (2015).
Ana Claudia Santos et al., "Nanocarriers for resveratrol delivery: Impact on stability and solubility concerns", *Trends in Food Science & Technology*, vol. 91, pp. 483-497 (2019).
Xiao Qian Pan et al., "Folate-conjugated pluronic/polylactic acid polymersomes for oral delivery of paclitaxel", *International Journal of Biological Macromolecules*, vol. 139, pp. 377-386 (2019).
Gregoriou et al., "Resveratrol loaded polymeric micelles for theranostic targeting of breast cancer cells", *Nanotheranostics*, vol. 5, pp. 113-124 (2021).
Melik-Nubarov et al., "Interaction of tumor and normal blood cells with ethylene oxide and propylene oxide block copolymers", *FEBS Letters*, pp. 194-198 (1999).
Batrakova et al., "Mechanism of Pluronic Effect on P-Glycoprotein Efflux System in Blood-Brain Barrier: Contributions of Energy Depletion and Membrane Fluidization", *The Journal of Pharmacology and Experimental Therapeutics*, vol. 299, No. 2, pp. 483-493 (2001).
Regev et al., "Membrane fluidization by ether, other anesthetics, and certain agents abolishes P-glycoprotein ATPase activity and modulates efflux from multidrug-resistant cells", *European Journal of Biochemistry*, vol. 259, pp. 18-24 (1999).
Chen et al., "PKD2 mediates multi-drug resistance in breast cancer cells through modulation of P-glycoprotein expression", *Cancer Letters*, vol. 300, pp. 48-56 (2011).

\* cited by examiner

*Primary Examiner* — Robert A Wax
*Assistant Examiner* — Quanglong N Truong
(74) *Attorney, Agent, or Firm* — Marshall, Gerstein & Borun LLP (57) ABSTRACT

A nanoparticle for treatment of cancer is provided comprising a poloxamer surfactant, a Vitamin E TPGS and an anticancer compound.

3 Claims, 7 Drawing Sheets

Figure 1 UV-vis spectra of Resveratrol, Pluronic F127, Vitamin E-TPGS, Res-NP and Empty NP

FIGURE 1

Figure 2: RES-NP size distribution

FIGURE 2

Figure 3: C6-NP size distribution

FIGURE 3

Figure 4: Similarity in size between C6-NP and RES-NP

THERAPEUTIC NANOCARRIER SYSTEM AND METHODS OF USE

BACKGROUND

The present invention relates to therapeutic nanocarrier systems for treatment of cancer and other diseases.

Breast cancer is one of the most frequently occurring cancers in women worldwide and it is estimated that 1 in 8 women in the United States will develop the disease at some point in their lives. The American Cancer Society estimates that in 2020 276,480 new cases of invasive breast cancer will be diagnosed in women in the United States alone. (American Cancer Society. How Common Is Breast Cancer? January 2020. Available at: jttps://www.cancer.org/cancer/breastcancer/about/how-common-is-breast-cancer.html. American Cancer Society. Cancer Facts & Figures 2020. Available at: https://www.cancer.org/content/dam/cancer-org/research/cancer-facts-and-statistics/annual-cancer-facts-and-figures/2020/cancer-facts-and-figures-2020.pdf. National Cancer Institute. BRCA Mutations: Cancer Risk and Genetic Testing. January 2018. Available at: https://www.cancer.gov/about-cancer/causes-prevention/genetics/brca-fact-sheet. American Cancer Society. Breast Cancer Risk Factors You Cannot Change. September 2019. Available at: http://www.cancer.org/cancer/breast-cancer/risk-and-prevention/breast-cancer-risk-factors-you-cannot-change.html.)

As defined via gene expression analysis, breast cancer is not a homogeneous disease but rather a combination of unique and distinctive subtypes. (Perou C M, Sψrlie T, Eisen M B, et al. Molecular portraits of human breast tumours. Nature 2000; 406:747-52.) These unique subtypes include, luminal A and luminal B subtypes, which are characterized by the expression of hormone receptors like the estrogen receptor (ER) or the progesterone receptor (PgR), and HER2 positive and the basal-like subtypes, which are less likely to express the ER or the PgR receptor. ER, PgR and HER2 cell-surface receptors are often exploited for the targeting of chemotherapeutic drugs to the cancerous tissue. In the absence of these receptors targeting becomes very problematic and results in poor prognosis and treatment. Triple-negative breast cancer: epidemiology and management options. (Dawood. 17, 2010, Drugs, Vol. 70, pp. 2247-5858. Triple negative breast cancer is a specific basal like subtype which is negative for all three markers—ER, PgR, and HER2.) 2. Sorlie T, Perou C M, Tibshirani R, et al. Gene expression patterns of breast carcinomas distinguish tumor subclasses with clinical implications. Proc Natl Acad Sci USA 2001; 98:10869-74. 3. Sψrlie T, Tibshirani R, Parker J, et al. Repeated observation of breast tumor subtypes in independent gene expression data sets. (Proc Natl Acad Sci USA 2003; 100:8418-23.) and accounts for 15-20% of all breast cancer cases (C. K. Anders and L. A. Carey, "Biology, metastatic patterns, and treatment of patients with triple-negative breast cancer," Clinical Breast Cancer, vol. 9, supplement 2, pp. S73-S81, 2009.)

Due to its unique biology triple negative breast cancer cannot utilize hormonal or anti-HER2 therapies rendering this type of cancer clinically challenging. Additionally, TNBC is highly aggressive and highly metastatic. (Anders C K, Carey L A. Biology, metastatic patterns, and treatment of patients with triple-negative breast cancer. Clin Breast Cancer. 2009; 9 Suppl 2(Suppl 2):S73-S81. doi:10.3816/CBC.2009.s.008) Current conventional treatments for breast cancer patients include chemotherapy, radiation and surgery. Kutanzi, K. R.; Yurchenko, O. V.; Beland, F. A.; Checkhun, V. F.; Pogribny, I. P. MicroRNA-mediated drug resistance in breast cancer. Clin. Epigenetics 2011, 2, 171-185. [CrossRef] [PubMed] Willers, H.; Würschmidt, F.; Janik, I.; Bünemann, H.; Heilmann, H. P.) Combined breast-preserving surgery, chemotherapy and radiotherapy in the treatment of breast carcinoma. (Strahlenther. Onkol. 1997, 173, 148-154.)

In current treatments chemotherapy is the most employed choice and although good chemotherapeutic candidates exist most fail to differentiate between healthy cells and malignant cells, resulting in systemic toxicity and severe side effects. It is therefore critical to develop more effective and less toxic strategies for the treatment of breast cancer. Phytochemicals, have been employed in breast cancer prevention and treatment with promising results. (D. Bonofiglio, C. Giordano, F. De Amicis, M. Lanzino, S. Ando, Natural products as promising antitumoral agents in breast cancer: mechanisms of action and molecular targets, Mini Rev. Med. Chem. 16 (2016) 596e604)

Of interest to the present invention is Resveratrol (Res), (trans-3,4',5-trihydroxystilbene, $C_{14}H_{12}O_3$) which is a plant-derived polyphenolic phytoalexin with potent biological activity. It is a non-flavonoid polyphenol found in abundancy in the skin of red grapes but has also been identified in other plant sources such as berries, soy beans, pomegranate and peanuts. Resveratrol has presented an array of medical benefits due to its interaction with a number of molecular targets. (B. Catalgol, S. Batirel, Y. Taga, N. K. Ozer, Resveratrol: French paradoxrevisited, Front. Pharmacol. 3 (2012) 141. A. Mobasheri, M. Shakibaei, Osteogenic effects of resveratrol in vitro: potential for the prevention and treatment of osteoporosis, Ann. N. Y. Acad. Sci. 1290 (2013) 59-66. G. M. Pasinetti, J. Wang, L. Ho, W. Zhao, L. Dubner, Roles of resveratrol and other grape-derived polyphenols in Alzheimer's disease prevention and treatment, Biochim. Biophys. Acta 1852 (2014) 1202-1208. A. Borriello, D. Bencivenga, I. Caldarelli, A. Tramontano, A. Borgia, V. Zappia, et al., Resveratrol: from basic studies to bedside, Cancer Treat. Res. 159(2014) 167-184. [31] B. B. Aggarwal, A. Bhardwaj).

For example, Resveratrol found in red wine has been notoriously linked to the 'French paradox' for its cardioprotective effects. Besides its cardioprotective effects resveratrol has also been examined for its anticancer properties. Consequently, there are a plethora of studies in the literature suggesting the use of Resveratrol as a chemopreventive and chemotherapeutic agent against various types of malignancies, including mammary. [31] B. B. Aggarwal, A. Bhardwaj, R. S. Aggarwal, N. P. Seeram, S. Shishodia, Y. Takada, Role of resveratrol in prevention and therapy of cancer: preclinical and clinical studies, Anticancer Res. 24 (2004) 2783-2840. [32] J. M. Pezzuto, Resveratrol as an inhibitor of carcinogenesis, Pharm. Biol. 46(2008) 443-573. [33] A. Bishayee, Cancer prevention and treatment with resveratrol: from rodent studies to clinical trials, Cancer Prev. Res. 2 (2009) 409-418. [34] A. Bishayee, T. Politis, A. S. Darvesh, Resveratrol in the chemoprevention and treatment of hepatocellular carcinoma, Cancer Treat. Rev. 36 (2010)43-53. [35] L. G. Carter, J. A. D'Orazio, K. J. Pearson, Resveratrol and cancer: focus on in vivo evidence, Endocr. Relat. Cancer 21 (2014) R209-R225. D. A. Benitez, E. Pozo-Guisado, A. Alvarez-Barrientos, P. M. Fernandez-Salguero, and E. A. Castell'on, "Mechanisms involved in resveratrol-induced apoptosis and cell cycle arrest in prostate cancer-derived cell lines," Journal of Andrology, vol. 28, no. 2, pp. 282-293, 2007. [59] A. C. Faber and T. C. Chiles, "Resveratrol induces apoptosis in transformed follicular lymphoma OCI- LY8 cells: evidence for a novel mechanism involving inhibition of BCL6 signaling," International Journal of Oncology, vol. 29, no. 6, pp. 1561-1566, 2006. [60] Y. Cao, Z.-D. Fu, F. Wang, H.-Y. Liu, and R. Han, "Antiangiogenic activity of resveratrol, a natural compound from medicinal plants," Journal of Asian Natural Products Research, vol. 7, no. 3, pp. 205-213, 2005.)

Resveratrol's potential against mammary carcinogenesis has been well established in the literature and has been linked to various cell signaling pathways which cause cell cycle arrest, induce apoptosis, suppress proliferation, reduce inflammation and angiogenesis, and inhibit metastasis. (Sinha, Dona & Sarkar, Nivedita & Biswas, Jaydip & Bishayee, Anupam. (2016). Resveratrol for breast cancer prevention and therapy: Preclinical evidence and molecular mechanisms. Seminars in Cancer Biology. 40-41. 10.1016/j.semcancer.2015.11.001. (B. B. Aggarwal, A. Bhardwaj, R. S. Aggarwal, N. P. Seeram, S. Shishodia, Y. Takada, Role of resveratrol in prevention and therapy of cancer: preclinical and clinical studies, Anticancer Res. 24 (2004) 2783-2840 [33] A. Bishayee, Cancer prevention and treatment with resveratrol: from rodent studies to clinical trials, Cancer Prev. Res. 2 (2009) 409-418.)

Additionally, Resveratrol behaves as a phytoestrogen and has been utilized in hormone-dependent therapy against ERα and PR subtypes of breast cancer. H. Mehdawi, M. Alkhalaf, I. Khan, Role of Na+/H+ exchanger in resveratrol-induced growth inhibition of human breast cancer cells, Med. Oncol. 29 (2012) 25-32.

Moreover, it has been shown that resveratrol enhances the cytotoxic efficacy of commonly used chemotherapeutic drugs Y. Ito, T. Mitani, N. Harada, A. Isayama, S. Tanimori, S. Takenaka, et al., Identification of carbonyl reductase 1 as a resveratrol-binding protein by affinity chromatography using 4_amino-3,5-dihydroxy-trans-stilbenes, J. Nutr. Sci. Vitaminol. 59 (2013) 358-364. such as doxorubicin, in the treatment of an array of cancers. A. M. Al-Abd, A. M. Mahmoud, G. A. El-Sherbiny et al., "Resveratrol enhances the cytotoxic profile of docetaxel and doxorubicin in solid tumour cell lines in vitro," Cell Proliferation, vol. 44, no. 6, pp. 591-601, 2011.

Besides the abundance of literature supporting the use of Resveratrol as a potent chemotherapeutic agent resveratrol exhibits poor clinical performance. This is due to the fact that Resveratrol displays poor water solubility, short half-life and chemical instability in vivo. Thus, achieving adequate bioavailability at an effective therapeutic dose in clinical studies has been the prevailing stasis to its clinical use. (J. M. Smoliga and O. Blanchard, "Enhancing the delivery of resveratrol in humans: if low bioavailability is the problem, what is the solution?" Molecules, vol. 19, no. 11, pp. 17154-17172, 2014. [55] R. Pangeni, J. K. Sahni, J. Ali, S. Sharma, and S. Baboota, "Resveratrol: review on therapeutic potential and recent advances in drug delivery," Expert Opinion on Drug Delivery, vol. 11, no. 8, pp. 1285-1298, 2014. J. M. Smoliga, O. Vang, and J. A. Baur, "Challenges of translating basic research into therapeutics: resveratrol as an example," Journals of Gerontology—Series A: Biological Sciences and Medical Sciences, vol. 67, no. 2, pp. 158-167, 2012.)

Of interest to the present invention is the use of poloxamer 407 block copolymer as a carrier for cancer applications because of its known anticancer potential. (Block copolymer-based formulations of doxorubicin effective against drug resistant tumours. Alakhov, V and Kabanov, A. 2002, Biomedical Polymers and Polymer Therapeutics, pp. 121-127. Pluronic block copolymers as novel polymer therapeutics for drug and gene delivery. Kabanov, A V, Batrakova, E V and Alakhov, V Y. 2-3, 2002, Journal of Controlled Release, Vol. 82, pp. 189-212. Hypersensitization of multidrug resistant human ovarian carcinoma cells by pluronic P85 block copolymer. Alakhov, V Y, et al. 2, 1996, Bioconjugate Chemistru, Vol. 7, pp. 2019-216. Effects of pluronic and doxorubicin on drug uptake, cellular metabolism, apoptosis and tumor inhibition in animal models of MDR cancers. Batrakova, E V, Li, S and Brynskikh, A M. 3, 2010, Journal of Controlled Release, Vol. 143, pp. 290-301. N. S Melik-Nubarov, O. O Pomaz, T Dorodnych, G. A Badun, A. L Ksenofontov, O. B Schemchukova, S. A Arzhakovinteraction of tumor and normal blood cells with ethylene oxide and propylene oxide block copolymers FEBS Lett., 446 (1999), pp. 194-198)

Also of interest to the present invention are nano drug delivery systems which have been utilized to circumvent the limitations associated with hydrophobic drug molecules like Resveratrol. A. C. Santos, F. Veiga, and A. J. Ribeiro, "New delivery systems to improve the bioavailability of resveratrol," Expert Opinion on Drug Delivery, vol. 8, no. 8, pp. 973-990, 2011. Nanomaterial-based carriers circumvent problems associated with stability, solubility and toxicity by offering protection from degradation, enabling controlled release and biodistribution and by increasing bioavailability through specific targeting Nguyen, T., et al., Designing a better theranostic nanocarrier for cancer applications. Nanomedicine, 2014. 9(15): p. 2371-2386. The development of biodegradable, polymer based NDDSs, specifically ones prepared from amphiphilic block copolymers, has gained considerable attention in recent years. Polymeric micelles are a promising approach as they spontaneously self-assemble into nano-sized aggregates. In general, amphiphilic block or graft copolymers composed of hydrophilic and hydrophobic segments can self-assemble into polymeric micelles at a concentration above their critical micelle concentration (CMC). Kumari A, Yadav S K, Yadav S C. Biodegradable polymeric nanoparticles based drug delivery systems. *Colloids* Surf B Biointerfaces. 2010; 75(1):1-18. doi:10.1016/j.colsurfb.2009.09.00111. Masood F. Polymeric nanoparticles for targeted drug delivery system for cancer therapy. Mater Sci Eng C. 2016; 60:569-578. doi:10.1016/j.msec.2015.11.067 Pro-apoptotic Properties of Chemopreventive Agents, Christiana M. Neophytou, Yiota Gregoriou, Andreas I. Constantinou, Pages 517-559.

Further of interest is Vitamin E TPGS, a synthetic derivative of natural alpha-tocopherol, is an FDA and EFSA approved pharmaceutical adjuvant frequently used in the development of DDS to improve the pharmacokinetics of anti-cancer drugs and reduce multi-drug resistance. D-alpha-tocopheryl polyethylene glycol succinate (TPGS) induces cell cycle arrest and apoptosis selectively in Survivin-overexpressing breast cancer cells. Neophytou, C M, et al. 2014, Biochem Pharmacology, Vol. 89, pp. 31-42.

Drug delivery innovations for enhancing the anticancer Potential of Vitamin E isoforms and their derivatives. Neophytou, C M and Constantinou, A. I. 2015, BioMed Research International, pp. 1-16. Additionally, TPGS has been shown to greatly enhance the performance of nanoparticles, resulting in much higher cellular uptake of the drug as well as more desirable in vivo pharmacokinetics. (New-concept chemotherapy by nanoparticles of biodegradable polymers: where are we now?. Feng, S S. 3, 2006, Nanomedicine (Lond), Vol. 1, pp. 297-309. In vitro and in vivo studies on vitamin E TPGS-emulsified poly(D,L-lactic-co-glycolic acid) nanoparticles for paclitaxel formulation. Win, K Y and Feng, S S. 10, Biomaterials, Vol. 27, pp. 2285-2291.

Enhanced cellular uptake and in vivo pharmacokinetics of rapamycin-loaded cubic phase nanoparticles for cancer therapy. Parhi, P, Mohanty, C and Sahoo, S K. 10, 2011, Acta Biomate, Vol. 7, pp. 3656-3669.)

Also of interest to the present invention are block copolymer-based formulations of doxorubicin effective against drug resistant tumours. Alakhov, V and Kabanov, A. 2002, Biomedical Polymers and Polymer Therapeutics, pp. 121-127. Pluronic block copolymers as novel polymer therapeutics for drug and gene delivery. Kabanov, A V, Batrakova, E V and Alakhov, V Y. 2-3, 2002, Journal of Controlled Release, Vol. 82, pp. 189-212. Hypersensitization of multidrug resistant human ovarian carcinoma cells by pluronic P85 block copolymer. Alakhov, V Y, et al. 2, 1996, Bioconjugate Chemistru, Vol. 7, pp. 2019-216. Effects of pluronic and doxorubicin on drug uptake, cellular metabolism, apoptosis and tumor inhibition in animal models of MDR cancers. Batrakova, E V, Li, S and Brynskikh, A M. 3, 2010, Journal of Controlled Release, Vol. 143, pp. 290-301.

Nevertheless, there remains an interest in the art for improved and more effective means of administering therapeutics and particularly anti-cancer therapeutics to human and non-human subjects.

SUMMARY OF THE INVENTION

The present invention provides useful nanoparticle compositions comprising a poloxamer surfactant, a Vitamin E TPGS and an anticancer compound.

Various poloxamer surfactant molecules can be used in the practice of the invention which will result in nanoparticles of different sizes and shapes but a particularly preferred poloxamer surfactant is Poloxamer 407 which is a triblock copolymer consisting of a central hydrophobic block of polypropylene glycol flanked by two hydrophilic blocks of polyethylene glycol (PEG). The approximate lengths of the two PEG blocks is 101 repeat units while the approximate length of the propylene glycol block is 56 repeat units. This particular compound is also known by the BASF trade name Pluronic F127 or by the Croda trade name Synperonic PE/F 127. Poloxamer 407 is particularly preferred as a surfactant because it exhibits anticancer properties when used in practice of the invention.

According to a preferred aspect of the invention the anticancer compound is resveratrol but it is contemplated that other anti-cancer therapeutics can be incorporated into the nanoparticles of the invention. In addition, the nanoparticles can comprise other agents such as labels and markers including flurophore compounds such as Coumanin 6 although those of skill in the art would recognize that a variety of other label and fluorophore compounds could be incorporated into the nanoparticles.

The size of the nanoparticle will vary according to the identity of the poloxamers surfactant and the proportions of the other components but will generally range from diameters of 100 nm to 200 nm with poloxamer 407 nanoparticles containing resveratrol having diameters of about 179±0.4 nm and poloxamer 407 nanoparticles containing Coumanin 6 having diameters of about 144±0.5 nm.

The nanoparticles may be used in methods of treating cancer comprising administering to a subject in need thereof a therapeutic composition comprising an effective amount of the nanoparticle. The nanoparticles containing poloxamers 6 and resveratrol are particularly useful for treatment of human breast cancer but it is contemplated that they will provide therapeutic effects for the treatment of other neoplastic diseases. It is further contemplated that nanoparticles comprising only one of a poloxamer surfactant or Vitamin E TPGS rather than both might be of use in the treatment of cancer.

DETAILED DESCRIPTION OF THE INVENTION

According to the present invention an optimized method for preparing a nanodelivery system for breast cancer made from poloxamer 407 (Pluronic F127 block copolymer), for the delivery of resveratrol, in vitro, using Vitamin E-TPGS as the emulsifier. The nanoparticle is unique because it comprises a combination of biodegradable and biocompatible materials with known anticancer properties. Moreover, the same type of nanoparticle can be applied to carry a fluorophore, such as Coumarin 6, offering the convenience of simultaneous diagnosis and therapy into a single nanoplatform.

Poloxamer 407 (Pluronic F127) is an amphiphilic triblock copolymer composed of poly(ethylene oxide) (PEO) and poly(propylene oxide) (PPO), PEO-x-PPO-y-PEO-x). Amphiphilic block copolymers self-assemble spontaneously in aqueous environments into polymeric nanostructures known as micelles and for this reason they have been commonly used to solubilize hydrophobic drugs in drug delivery. The PEO block of F127 is hydrophilic and forms the outside layer of the nanoparticle and the PPO block is hydrophobic and composes the inner core. The hydrophobic core serves as a reservoir in which the hydrophobic drug molecule can be incorporated and protected from inactivation in biological media so it can be delivered effectively to the malignancy while the hydrophilic shell promotes the delivery of the drug to target cells. Kataoka K, Kwon G, Yokoyama M, Okano T, Sakurai Y. Block copolymer micelles as vehicles for drug delivery. J Control Release. 1992; 24:119-132.18. Kumari A, Yadav S K, Yadav S C. Biodegradable polymeric nanoparticles based drug delivery systems. Colloids Surf B. 2010; 17:1-18.doi:10.1016/j.colsurfb.2009.09.00119. Imran M, Shah M R, Shafiullah. Chapter 10—Amphiphilic block copolymers—based micelles for drug delivery. In: Grumezescu A M, editor. Design and Development of New Nanocarriers. Norwich: William Andrew Publishing; 2018:365-400.

Pluronic®F127 has attracted a lot of attention in drug delivery because of its low toxicity in the body and the ability to encapsulate hydrophobic agents. Additionally, Pluronic F127 enhances proapoptotic signaling, thereby sensitizing tumour cells and making them more vulnerable to the effects of anticancer drugs. Block copolymer-based formulations of doxorubicin effective against drug resistant tumours. Alakhov, V and Kabanov, A. 2002, Biomedical Polymers and Polymer Therapeutics, pp. 121-127.

Poloxamer 407 is an amphiphilic triblock copolymer composed of poly(ethylene oxide) (PEO) and poly(propylene oxide) (PPO), PEO-x-PPO-y-PEO-x). Amphiphilic block copolymers self-assemble spontaneously in aqueous environments into polymeric nanostructures known as micelles and for this reason they have been commonly used to solubilize hydrophobic drugs in drug delivery. The PEO block of poloxamer 407 is hydrophilic and forms the outside layer of the nanoparticle and the PPO block is hydrophobic and composes the inner core.

The hydrophobic core serves as a reservoir in which the hydrophobic drug molecule can be incorporated and protected from inactivation in biological media so it can be delivered effectively to the malignancy while the hydrophilic shell promotes the delivery of the drug to target cells. Kataoka K, Kwon G, Yokoyama M, Okano T, Sakurai Y. Block copolymer micelles as vehicles for drug delivery. J Control Release. 1992; 24:119-132.18. Kumari A, Yadav S K, Yadav S C. Biodegradable polymeric nanoparticles based drug delivery systems. Colloids Surf B. 2010; 17:1-18.doi: 10.1016/j.colsurfb.2009.09.00119. Imran M, Shah M R, Shafiullah. Chapter 10—Amphiphilic block copolymers-based micelles for drug delivery. In: Grumezescu A M, editor. Design and Development of New Nanocarriers. Norwich: William Andrew Publishing; 2018:365-400 Pluronic block copolymers as novel polymer therapeutics for drug and gene delivery. Kabanov, A V, Batrakova, E V and Alakhov, V Y. 2-3, 2002, Journal of Controlled Release, Vol. 82, pp. 189-212. Hypersensitization of multidrug resistant human ovarian carcinoma cells by pluronic P85 block copolymer. Alakhov, V Y, et al. 2, 1996, Bioconjugate Chemistru, Vol. 7, pp. 2019-216. Effects of pluronic and doxorubicin on drug uptake, cellular metabolism, apoptosis and tumor inhibition in animal models of MDR cancers. Batrakova, E V, Li, S and Brynskikh, A M. 3, 2010, Journal of Controlled Release, Vol. 143, pp. 290-301. And is known to induce drastic changes in the microviscosity of cell membranes of cancerous cells N. S Melik-Nubarov, O. O Pomaz, T Dorodnych, G. A Badun, A. L Ksenofontov, O. B Schemchukova, S. A Arzhakovinteraction of tumor and normal blood cells with ethylene oxide and propylene oxide block copolymers FEBS Lett., 446 (1999), pp. 194-198.

Vitamin E TPGS, a synthetic derivative of natural alpha-tocopherol used in the formulation of the nanoparticles is an FDA and EFSA approved pharmaceutical adjuvant frequently used in the development of DDS to improve the pharmacokinetics of anti-cancer drugs and reduce multi-drug resistance.

Example 1

According to this example a nanoformulation was synthesized and subsequently characterized by particle size, morphology, encapsulation efficiency (EE %) and drug loading (DL %). Additionally, the formulation's performance as a diagnostic and therapeutic agent was evaluated by a cellular uptake assay and an in vitro cytotoxicity assay in the breast cancer MCF7 cell line and the triple negative breast cancer MDA-MB-231 cell line as well as in human normal breast MCF 10 A cells. The nanoparticle showed high EE % and DL % of RSV and coumarin-6 and showed superior uptake in breast cancer cells compared to normal cells rendering this nanoparticle as a good candidate for diagnosis and therapy of difficult to treat mammary malignancies.

Resveratrol was purchased from Selleck chemicals (Dallas, Tex., USA). The purity as determined by HPLC was 99.73%. Pluronic F-127 was purchased from Sigma-Aldrich (St. Louis, Mo., U.S.A), coumarin 6 (MW 350.43) from Santa Cruz Biotechnology (Dallas, Tex., USA) and D-Alpha Tocopheryl Polyethylene Glycol 1000 Succinate (Vitamin E TPGS) from Eastman Chemical Company (Kingsport, Tenn., USA). Acetone (ACS grade) and Dichloromethane anhydrous (purity≥99.8%) were purchased from Sigma-Aldrich and Dimethyl Sulfoxide, extra pure (99.9%) from Scharlau chemicals (Barcelona, Spain).

Example 2

The resveratrol-loaded nanoparticles were prepared by the single-emulsion method. The preparation method comprises: mixing F127-Pluronic (EO106PO70EO106, MW=12,600) with dichlomethane as the solvent and D-alpha-tocopheryl polyethylene glycol 1000 succinate (Vitamin E-TPGS,) as the emulsifier. More specifically, 100 mg of PF127 were mixed in 1 mL of dichloromethane and 50 µl of resveratrol in acetone (at a concentration of 50 mg/mL) were added to the polymer mixture by vortexing until the encapsulant was homogeneously dispersed. The polymer/encapsulant solution was then added swiftly to Vitamin E-TPGS at a ratio of 1:2 on high vortex. The resulting oil-in-water emulsion was ultrasonicated (Misonix, Ultrasonic Liquid Processors) in three 10 sec bursts (50% amplitude) on ice to induce nanosized droplets. The emulsion was then transferred into a beaker containing 45 mL of Vitamin E-TPGS and stirred for 3 hrs to evaporate the solvent. The resulting hardened nanoparticles are then recovered by centrifugation on a fixed rotor at 17,000 rcf for 15 min at 22° C. (Cientec CT-15000R centrifuge). The nanoparticle pellet is washed 3 times with distilled water to remove any unentrapped drug. The supernatant containing unentrapped drug and unused polymer was collected and further tested to determine the drug entrapment efficiency of the nanoparticle. The resulting nanoparticle suspension was transferred to 15 mL pre-weighed falcon tubes, cooled to −80° C. for 3 hours and freeze-dried for 48 hrs.

For coumarin-6 loaded nanoparticles, coumarin-6 was added as the drug in place of Resveratrol. Coumarin-6 was added directly to the polymer solution at a polymer to drug ratio of 1:40. The fabrication steps following were performed in the same manner as in the case of Res-loaded nanoparticles and as mentioned above and the encapsulation efficiency of the Coumarin-6 loaded nanoparticles was 78%.

The freeze-dried nanoparticles were wrapped in foil and stored at 4° C. until further use. The freeze dried nanoparticles were resuspended in ultrapure water (Sartorius Arium 611 VF Water Purifier system) and the solution was sonicated in a water bath sonicator (RS Pro, ultrasonic cleaner) three times for 15 min each time and subsequently filtered through a 0.45 µm syringe filter ((PTFE, Hydrophilic, Dissolution Accessories, (Oosterhout, The Netherlands)) to remove all aggregates and obtain nanoparticles of uniform size prior to use.

Analysis of Size and Morphology

Scanning Electron Microscopy

The morphological examinations were made with Scanning Electron Microscopy. Samples were mounted on aluminum specimen stubs and gold-sputtered to 5 nm thick films to prevent beam charging effects (SC7640 Sputter coater, Quorum Technologies, Kent, UK). High resolution scanning electron microscopic analysis was performed at 20.00 kV (magnification range of 30,000-120,000×) using a FEI Quanta 200 (FEI, Oregon, USA) microscope and images were processed using the ImageJ software.

Tunable Resistive Pulse Sensing (TRPS) Size Analysis

Quantification and size analysis of nanoparticles was performed using the qNano Gold platform (Izon Science, Oxford, U.K.). Nanoparticles were diluted in filtered PBS, measured using the nanopore NP200 (Izon Science, Oxford, U.K.) and compared to calibration particles CPC200. Data analysis was carried out using the Izon Control Suite software v3.3 (Izon Science, Oxford, U.K.).

Size and zeta potential (surface charge) of NPs were measured at least in triplicate.

Composition Analysis by UV-Vis

The composition of the nanoparticles was verified by UV-Vis spectrophotometry (Perkin Elmer Lambda 1050, USA). For this purpose the UV-Vis spectra of pure resveratrol, pure F127, pure TPGS, resveratrol loaded-NPs and empty nanoparticles were attained. The samples were scanned at a wavelength of 250-850 nm. All solids and lyophilized nanoparticles were dissolved in DMSO prior to analysis.

Determination of the Encapsulation Efficiency and Drug Loading Content

The percent Encapsulation Efficiency (EE %) and the percent Drug Loading (DL %) content of Res loaded nanoparticles was determined by analyzing the supernatant obtained from the washes during synthesis (un-encapsulated drug) against a standard calibration curve of pure resveratrol.

A representative 2 ml sample from each wash was centrifuged at 10 000 r.p.m. for 10 min at room temperature. The supernatant was collected and analyzed on a multimodal microplate reader (Tecan Spark 20M) to measure the fluorescence intensity of the sample (excitation wavelength of 356 nm and an emission wavelength of 383 nm). For the calibration curve pure resveratrol was first diluted in DMSO to form a stock solution. This was further diluted in PBS to form a series of concentrations for the calibration curve.

All experiments were performed in triplicates.

The % entrapment efficiency (EE %) is calculated from equation (1)

$$EE(\%) = \frac{C1}{C2} \times 100\% \qquad \text{eqn (1)}$$

The % drug loading content (DL %) is calculated from equation (2)

$$DL(\%) = \frac{C1}{C2 + C3} \times 100\%, \qquad \text{eqn (2)}$$

where C1 is the amount of RSV encapsulated in RSV-PLGA-NPs, C2 is the total amount of RSV used during synthesis and C3 is the total amount of polymer used during synthesis.

Cell Culture and Reagents

MCF-7, MDA-MB-231 and MCF-10A cell lines were obtained from the American Type Culture Collection (ATCC) (Manassas, Va.). MCF10CA1a (MIV) breast cancer cells expressing the luciferase gene (MIV-Luc) were obtained from the Karmanos Cancer Institute (Detroit, Mich., USA) and were used as a negative control in all experiments since they do not display any green autofluoresence. MCF-7 and MDA-MB-231 breast cancer cell lines were cultured in DMEM supplemented with 10% fetal bovine serum (FBS) and 1% antibiotic/antimycotic. MCF-10A immortalized breast cell line and MIV-Luc cell line were cultured in DMEM F12 supplemented with 20 ng/ml EGF, 100 ng/ml Cholera Toxin, 500 ng/ml Hydrocortizone, 10 μg/ml Insulin, 5% Horse Serum (HS) and 1% antibiotic/antimycotic. Sub culturing of the cells was performed using 0.25% trypsin. The RPMI, FBS, antibiotics and trypsin used in cell culture were purchased from Gibco, Invitrogen (Carlsbad, Calif., USA).

In Vitro Cellular Uptake

Flow Cytometry

Considering that resveratrol is a non-fluorescent drug, coumarin-6 was incorporated as a fluorescent dye during nanoparticle formulation to study the cellular uptake of the nanoparticle in three cell lines, MCF-7, MDA-MB-231 and MCF-10A. MCF-7, MDA-MB-231, MCF-10A and MIVLuc cell lines were seeded in 6-well plates ($2 \times 10^5$/well) and incubated with 250 μg/ml of C-6 NP for 30, 60, 120 and 240 minutes. At the end of each incubation time point, cells were washed 3 times with PBS, harvested with trypsin and centrifuged for 5 minutes at 1100 rpm. Following supernatant aspiration, the cells were resuspended in 500 μl of PBS prior FACs analysis. Data were acquired on a Bio-Rad S3e Cell Sorter flow cytometer and analyzed using FlowJo software (Treestar). Each experiment was repeated three times.

Fluorescence Microscopy

To evaluate the cellular uptake of NPs in MCF-7, MDA-MB-231 and MCF-10A cell lines, a fluorescent dye coumarin-6 (C6) was used as a marker and was therefore encapsulated in the nanoparticles instead of Resveratrol. Cells were seeded in 6-well plates at a density of $2 \times 10^5$ cells per well with coverslips and incubated overnight to allow for cell attachment. Cells were treated with 250 mg/mL of C-6 NP and incubated for 30 and 240 minutes. At the end of the incubation, cells were washed 3 times with PBS, fixed with 4% paraformaldehyde (PFA) for 10 minutes. Cells were washed 4 times with PBS. To quench auto-fluorescence coverslips were incubated with 1M ammonium chloride for 15 minutes. Next, the coverslips were washed 3 times with PBS and mounted with DAPI mounting medium (Invitrogen/Thermo Fisher Scientific, Grand Island, N.Y. USA).

MTT Assay

A total of $5 \times 10^4$ cells/mL were seeded per well of a 96-well plate and incubated overnight to allow for cell attachment and recovery. At the end of each incubation period, cells were treated with different concentrations of Resveratrol alone or with the representative nanoparticles for the concentrations and time points described in the figure legends. Cell viability was measured using the MTT 3-(4, 5-dimethylthiazol-2-yl)-2,5-monotetrazolium bromide assay. At the end of each incubation period, 20 μl of MTT dye (1 mg/ml; Sigma St. Louis, Mo.) was added in each well and the plate was incubated at 37° C. for 4 hours. Subsequently, the plates were read on a microplate reader (Wallac, PerkinElmer, Massachusetts, USA) at 570 nm. Absorbance was proportional to the number of viable cells per well.

Percentage of cell viability in each group was calculated after normalization to its own control. All data are presented as mean values±standard deviation and representative for at least two independent experiments performed in triplicates. A p value of 0.05 was considered significant.

2.18. Statistical Analysis

The data were expressed as the mean±standard deviation (s.d.). Data analysis was carried out by GraphPad Prism v. 6.01 (GraphPad Software) and Origin Lab OriginalPro v. 8.5.1.

Results and Discussion

Synthesis and Characterization of NPs

Resveratrol was encapsulated by Pluronic F127 to improve its water solubility and enhance its stability, thereby improving its pharmacological potential. Additionally, Coumarin-6 was encapsulated in the same manner for diagnostic purposes. Both nanoparticles were prepared by a modified single emulsion method (McCall, R. L., Sirianni, R. W. PLGA Nanoparticles Formed by Single- or Double-emulsion with Vitamin E-TPGS. J. Vis. Exp. (82), e51015, doi:10.3791/51015 (2013)) using dichloromethane (DCM) as the solvent and vitamin E-TPGS as the emulsifying agent. Vitamin E-TPGS is a superior stabilizing agent offering improved emulsification, superior encapsulation efficiency as well as rendering proapoptotic properties thereby adding to the anticancer capability of the nanoparticle. The resulting nanoparticle forms via the spontaneous self-assembly of pluronic F127 at or above its critical micelle concentration (CMC) of around 0.1% (w/v). (P. K. Sharma and S. R. Bhatia, "Effect of anti-inflammatories on Pluronic® F127: micellar assembly, gelation and partitioning," International Journal of Pharmaceutics, vol. 278, no. 2, pp. 361-377, 2004. View at: Publisher Site|Google Scholar) J. J. Escobar-Chávez, M. López-Cervantes, A. Naïk, Y. N. Kalia, D. Quintanar-Guerrero, and A. Ganem-Quintanar, "Applications of thermo-reversible pluronic F-127 gels in pharmaceutical formulations," Journal of Pharmacy and Pharmaceutical Sciences, vol. 9, no. 3, pp. 339-358, 2006. View at: Google Scholar A. V. Kabanov, P. Lemieux, S. Vinogradov, and V. Alakhov, "Pluronic® block copolymers: novel functional molecules for gene therapy," Advanced Drug Delivery Reviews, vol. 54, no. 2, pp. 223-233, 2002. View at: Publisher Site|Google Scholar.

The resulting structure consists of a core-shell arrangement. The hydrophobic inner core carries the drug and involves the PPO hydrophobic segment of the polymer and the tocopherol segment of Vitamin E-TPGS. The hydrophilic shell which surrounds the core is made of the hydrophic PEO segment of the polymer and the PEG chains of Vitamin E-TPGS. The hydrophilic shell renders the nanoparticle water soluble and enables the delivery of the hydrophobic drug in biological media. Our carrier system is unique because all its constituents are non-toxic, biocompatible and biodegradable. Additionally, most of the constituents have shown promising anti-cancer properties. To the best of our knowledge this is the first time such a combination of materials has been combined into a single platform.

Figure 1:
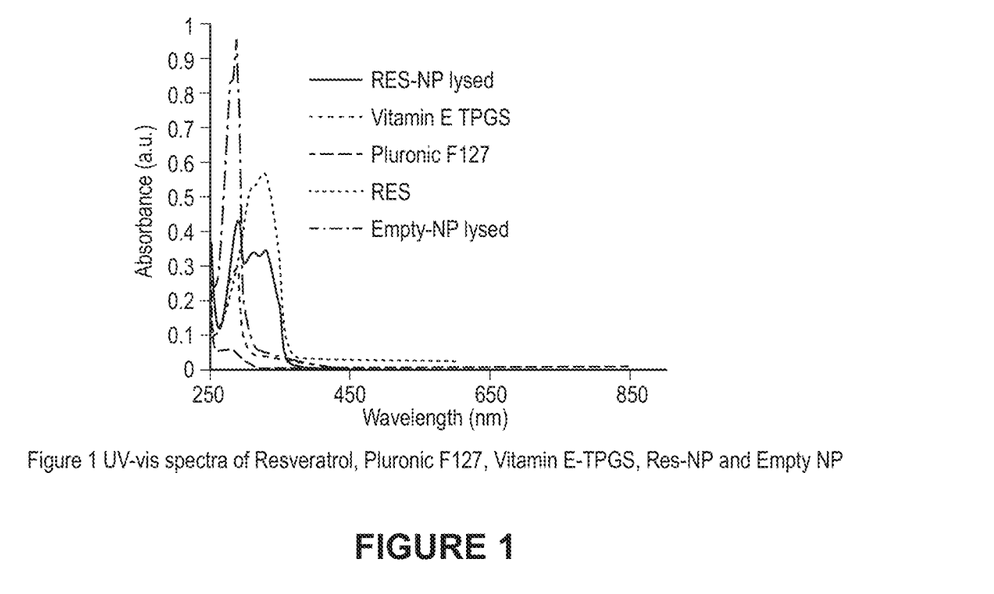
FIG. 1 depicts the UV spectra of nanoparticles containing Resveratrol, Pluronic F127, Vitamin E-TPGS, Res-NP and Empty NP.

The content of the nanoparticle was verified by UV-Absorption Spectroscopy. FIG. 1 shows the UV spectra of Pluronic-F127, Resveratrol and Vitamin E-TPGS as well as the spectra of RES loaded and empty nanoparticles. Resveratrol-loaded NPs exhibit an absorbance peak at 318 nm characteristic of resveratrol which is absent in the empty nanoparticle spectrum confirming the presence of resveratrol in the nanoparticle. (In FIG. 1 Resveratrol shows a characteristic absorption peak at around 318 nm. Abbreviations: RES is resveratrol, RES-NP implies Resveratrol loaded nanoparticle and Empty-NP implies empty nanoparticle.)

Characterization of the Nanoparticle

Size Analysis by TRPS

Figure 2:
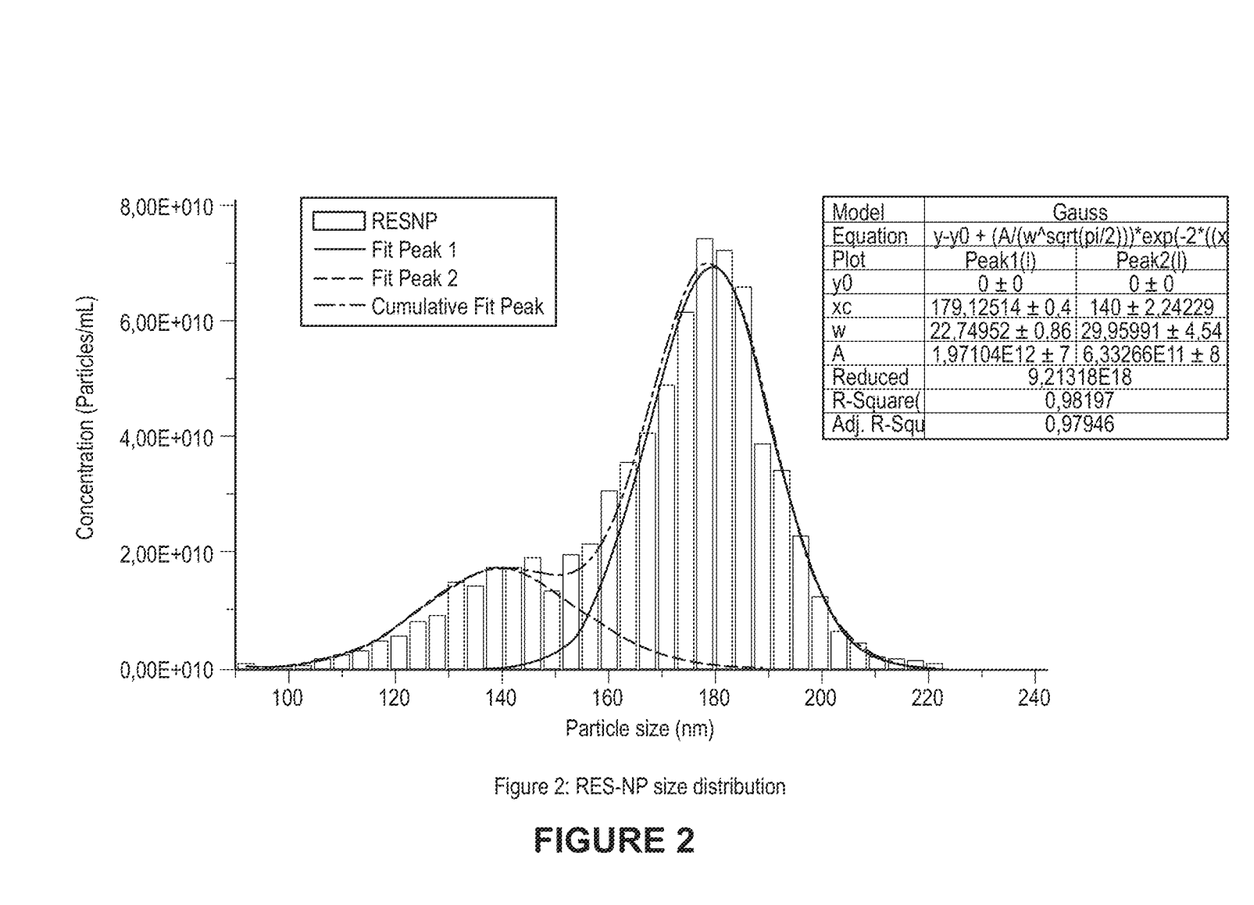
FIG. 2 depicts the size distribution of resveratrol loaded nanoparticles.
Figure 3:
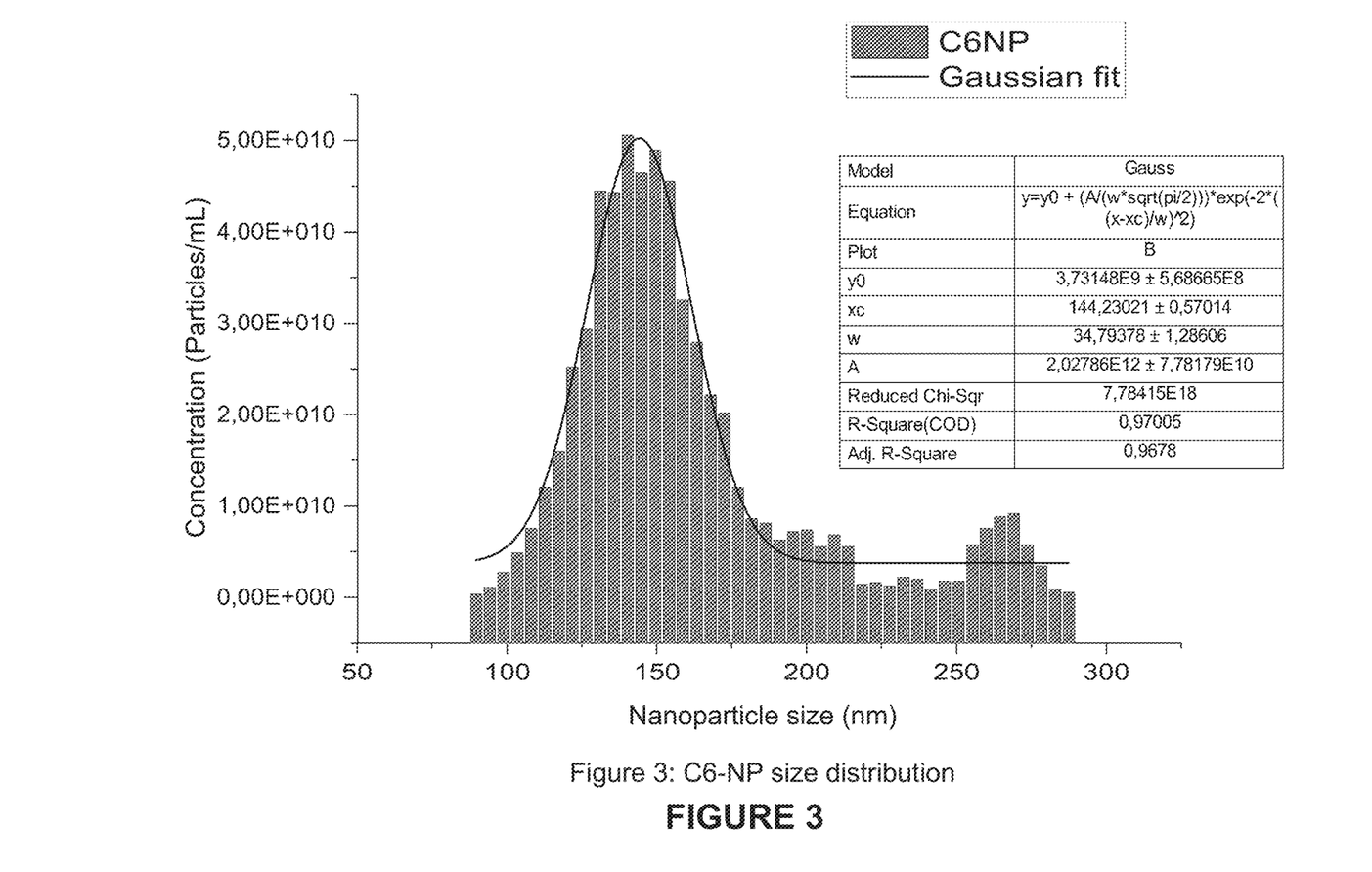
FIG. 3 depicts the size distribution of coumarin-6 loaded nanoparticles.

The size, mean concentration and surface charge of the nanoparticles were determined by q-nano. The measured mean concentration was $7.24 \times 10^{10}$ particles/mL as shown in FIGS. 2 and 3. Resveratrol loaded nanoparticles appear to possess two size populations. In FIG. 2 the mean particle diameter was 179±22 nm and 140±30 nm.

Figure 4:
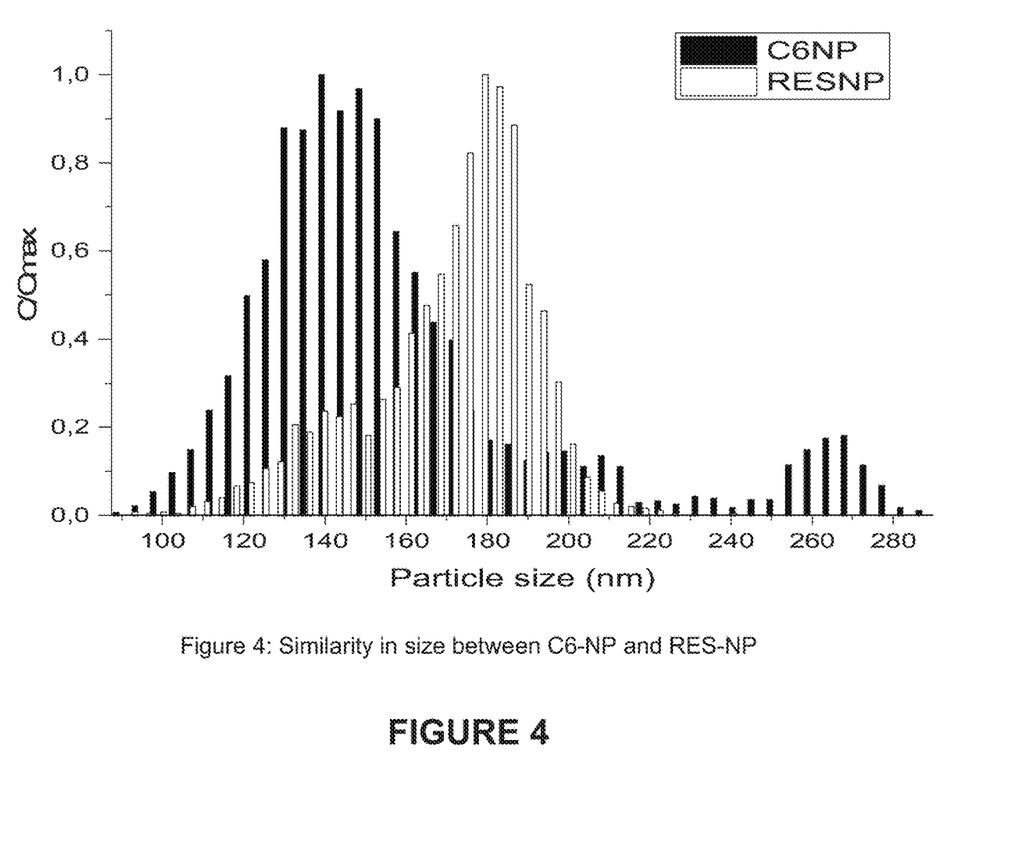
FIG. 4 depicts a comparison of the size distribution of resveratrol and coumarin loaded nanoparticles.

The mean particle diameter of Coumarin-6 loaded nanoparticles in FIG. 3 was 144±34 nm and the measured mean concentration was $2.73 \times 10^{10}$ particles/mL. The similarity in size between the two types of nanoparticles can be seen in FIG. 4.

The dependency of nanoparticle size with nanoparticle physicochemical characteristics is well established in the literature.

Size determines the overall therapeutic efficacy of the nanoformulation by regulating nanoparticle biodistribution and tumor penetration as well as cellular internalization. Moreover, size governs nanoparticle clearance from the blood and excretion from body. Over the past few decades a consensus has been reached in regards to the desired size for cancer applications. If only in view of size variances nanoparticles ranging from 100 nm to 200 nm are preferred due to their extended blood circulation and the relatively slow rate of uptake by the Resveratrol allowing for improved therapeutics. (Moghimi, S. M.; Hunter, A. C.; Andresen, T. L., Factors Controlling Nanoparticle Pharmacokinetics: An Integrated Analysis and Perspective. Annu Rev Pharmacol 2012, 52, 481-503. Consequently, most clinically approved nanoformulations for cancer applications have sizes in the range of 100 to 200 nm. Uster P S, Working P K, Vaage J. Pegylated liposomal doxorubicin (DOXIL®, CAELYX®) distribution in tumour models observed with confocal laser scanning microscopy. Int J Pharm. 1998; 162(1-2):77-86. [Google Scholar] 9. Gradishar W J, et al. Phase III trial of nanoparticle albumin-bound paclitaxel compared with polyethylated castor oil-based paclitaxel in women with breast cancer. J Clin Oncol. 2005; 23(31):7794-7803. [PubMed] [Google Scholar])

Figure 5A:
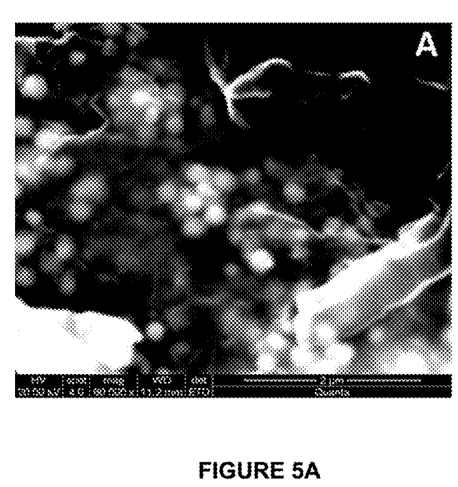
FIGS. 5A, and 5B depict scanning electron microscope images of the resveratrol loaded nanoparticles.
Figure 5B:
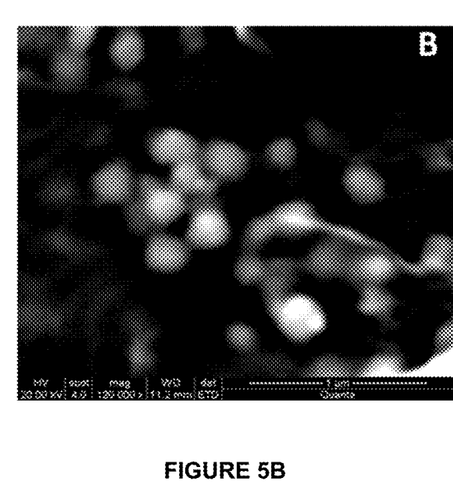
Figure 6:
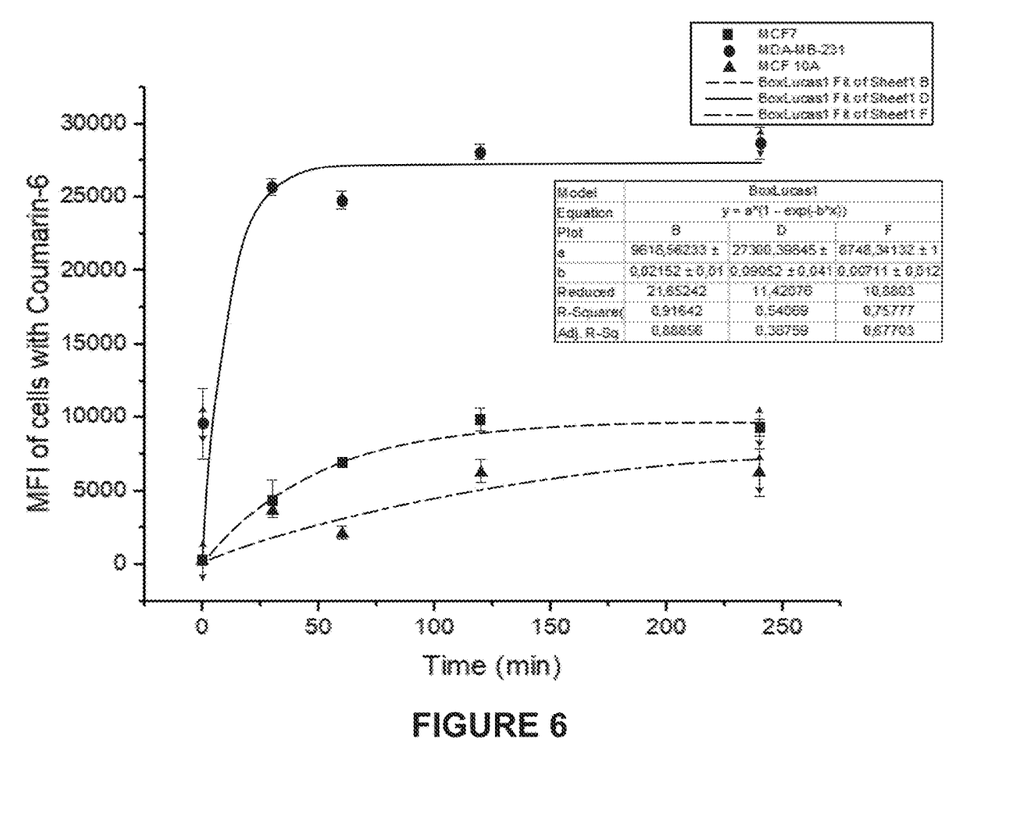
FIG. 6 depicts uptake by carcinogenic and normal cells.

The newly synthesized nanoformulation Res-load NP satisfies the above size credential and is therefore ideal for biological applications. The morphology of resveratrol loaded nanoparticles was examined by SEM. As shown in FIGS. 5A and 5B the nanoparticles exhibit spherical shape with a smooth surface. The size as determined by SEM was estimated to be 184.42±38 nm.

Table 1:

Determination of the Encapsulation Efficiency and Drug Loading Content

The entrapment efficiency and the drug loading content of Res-loaded NP are shown in table 1. The % entrapment efficiency was found to be 73±0.9 and the % drug loading content is 6.2±0.1. The results indicate that resveratrol was successfully loaded within the core of the nanoparticle.

TABLE 1

Characterization of nanoparticles. The size, drug loading content, and entrapment efficiency of the nanoparticles. Data is represented as mean ± SD ( n = 3).

| Nanoparticle Type | Mean Diameter (nm) | Entrapment efficiency (%) | Loading content (%) |
|---|---|---|---|
| Res-loaded | 179 ± 22 nm and 140 ± 30 nm | 73 ± 0.9 | 6.2 ± 0.1 |
| C-6-loaded | 144 ± 34 nm | 78 | |

Cellular Uptake by Flow Cytometry

Characterization of Nanoparticle Uptake in MDA-MB-231, MCF 7 and MCF 10 A Using Coumarin-6 as a Model Drug Cellular Uptake by Flow Cytometry Fluorescence microscopy of cells treated with coumarin-6 loaded nanoparticles was carried out and demonstrated that the uptake by carcinogenic cells is much more significant than in MCF10A (normal cells). Nuclear staining (DAPI) was compared with coumarin-6 staining at 20× magnification. Specifically, MCF-10A, MCF-7 and MDA-MB-231 cells were treated with 250 μg/mL of coumarin 6 NPs for 30 minutes and 240 minutes. Green fluorescence was observed in the cytoplasm around the nuclei of cells, suggesting uptake of coumarin 6 loaded NPs. Images (not shown) suggest that the uptake of coumarin 6 nanoparticles was much more significant in MCF 7 and MDA-MB-231 cells compared to healthy MCF10 A.

It should be noted that the concentration here (250 μg/ml) takes account the whole nanoparticle not just the load which is about ⅒th of that.

Cytotoxicity assays by MTT

Figure 7A:
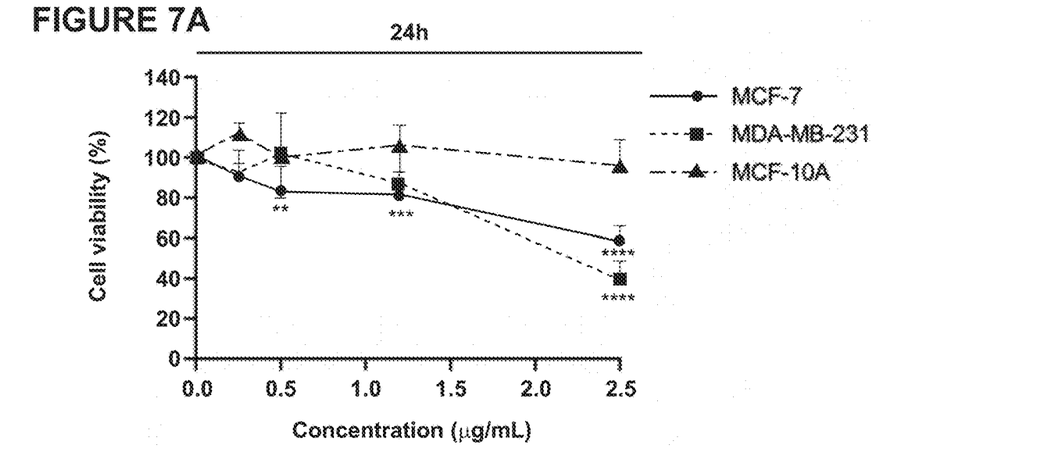
FIGS. 7A, 7B and 7C depict cytotoxicity of the therapeutic nanoparticles in MCF7 and MDA 231 cancer cell lines but that the nanoparticles have no significant effect on normal MCF 10A cell lines.
Figure 7B:
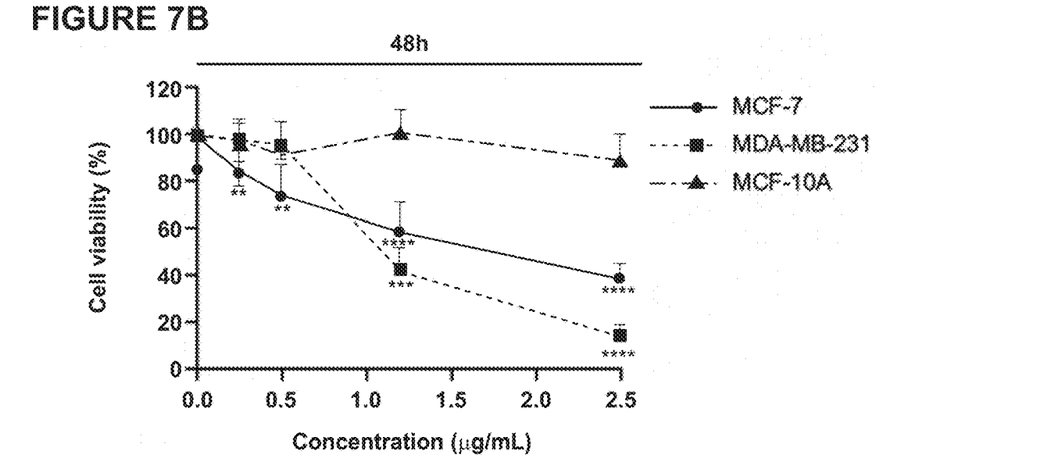
Figure 7C:
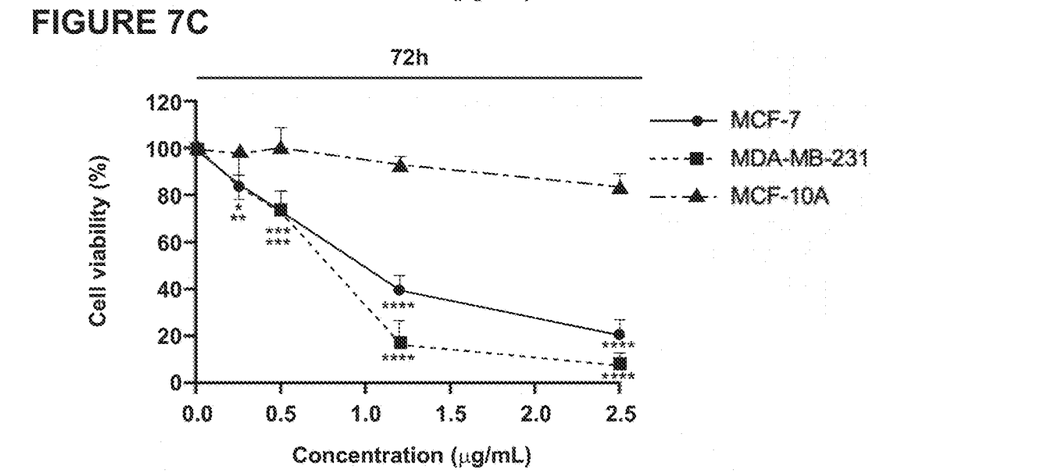

FIGS. 7A, 7B and 7C show that resveratrol loaded nanoparticles reduce cell viability in MCF7 and MDA 231 but have no significant effect on normal MCF 10A. They show specificity against cancer cells similar to what is observed in the uptake experiments. FIG. 7 depicts the % cell viability vs. concentration (μg/mL) plot for res-loaded nanoparticles. The anti-proliferative effect of res-loaded nanoparticles on MCF-10A, MCF-7 and MDA-MB-231 cell lines was examined at concentrations and time points as indicated: (A) treated for 24 h, (B) treated for 48 h and (C) treated for 72 h. All data are presented as mean values±standard deviation and are representative of at least two independent experiments performed in triplicate. P values: *<0.05, <0.01, *<0.001,****<0.0001 relative to control.

Cytotoxicity assay at 24, 48 and 72 hrs after incubation of cells lines MCF 7, MDA-MB-231 (cancer cell lines) and MCF10A (normal mammary cells) with various drug concentrations (0.25-2.5 ug/mL). The viability of MCF 10A normal cells is not affected by the nanoparticle whereas the viability of the cancer cells is greatly affected. (Note: These concentrations were based only on the resveratrol inside the nanoparticle. 2.5 μg/ml.)

Table 2.

TABLE 2

| | $IC_{50}$ | | |
|---|---|---|---|
| | 24 h | 48 h | 72 h |
| MDA-MB-231 | 2.32 ± 0.12 | 1.06 ± 0.12 | 0.76 ± 0.04 |
| MCF-7 | N/A | 1.61 ± 0.57 | 0.93 ± 0.09 |
| MCF-10A | N/A | N/A | N/A |

$IC_{50}$ values of res-loaded nanoparticles for all cell-lines at 24 h, 48 h and 72 h. $IC_{50}$ values were calculated using the Graph Pad Prism 8.0 (Graph Pad Software Inc., San Diego, CA, USA).
N/A is used in cases where cell viability did not reach 50%.

Numerous modifications and variations in the practice of the invention are expected to occur to those skilled in the art upon consideration of the foregoing description on the presently preferred embodiments thereof. Consequently, the only limitations which should be placed upon the scope of the present invention are those that appear in the appended claims.

What is claimed is:

1. A nanoparticle comprising a poloxamer surfactant, a Vitamin E TPGS and an anticancer compound wherein the poloxamer surfactant is poloxamer 407 and the anticancer compound is resveratrol which further comprises a fluorophore.

2. The nanoparticle of claim 1 wherein the particle has a diameter ranging from 100 nm to 200 nm.

3. A method of treating cancer comprising administering to a subject in need thereof a therapeutic composition comprising an effective amount of nanoparticle comprising a poloxamer surfactant, a Vitamin E TPGS and an anticancer compound wherein the poloxamer surfactant is poloxamer 407 and the anticancer compound is resveratrol wherein the cancer to be treated is triple negative breast cancer.

* * * * *